(12) United States Patent
Lovley et al.

(10) Patent No.: US 7,498,155 B2
(45) Date of Patent: Mar. 3, 2009

(54) MICROBIAL NANOWIRES, RELATED SYSTEMS AND METHODS OF FABRICATION

(75) Inventors: Derek R. Lovley, Leyden, MA (US); Gemma Reguera, Granby, MA (US); Kevin D. McCarthy, South Hadley, MA (US); Mark T. Tuominem, Shutesbury, MA (US)

(73) Assignee: University of Massachusetts, Amherst, MA (US)

( * ) Notice: Subject to any disclaimer, the term of this patent is extended or adjusted under 35 U.S.C. 154(b) by 0 days.

(21) Appl. No.: 11/371,775

(22) Filed: Mar. 9, 2006

(65) Prior Publication Data
US 2006/0257985 A1 Nov. 16, 2006

Related U.S. Application Data (60) Provisional application No. 60/659,917, filed on Mar. 9, 2005.

(51) Int. Cl.
*C12P 21/04* (2006.01)
(52) U.S. Cl. .................. 435/71.2; 435/41; 435/243
(58) Field of Classification Search .................. 435/71.2
See application file for complete search history.

(56) References Cited

OTHER PUBLICATIONS

TIGR Annotation Display GSU_1496 http:/cmr.tigr.org/tigr-scripts/CMR/shared/GenePageIdentity.cgi?tigr_locus=GSU_1496.*
Bond et al, Electricity Production by Geobacter sulferreducens attached to electrodes, Appled and environmental Microbiology, 2003, col. 69, p. 1548-1555.*
Childers et al., Geobacter metallireducens Accesses Insoluble Fe(III) oxide by Chemotaxis, Nature, Apr. 2002, vol. 416, p. 767-769.
Audette et al., DNA-binding Protein Nanotubes: Learning from Nature's Nanotech Examples, Nano Letters, 2004. vol. 4, p. 1897-1902.
Esteve-Nunez et al., Preferential Reduction of Fe(III)over Fumarate by Geobacter sulfurreducens, Journal of Bacteriology, May 2004, p. 2897-2899.
Reguera et al., Nanowires, Capacitors, and Other Novel Electron Transfer Mechanisms in Geobacter Species Elucidated from Genome-Scale Investigation, USDOE Genomes to Life Contractor-Grantee Workshop III, Feb. 6-9, 2005, Washington, DC.
Methe et al., Genome of Geobacter sulfurreducens: Metal Reduction in subsurface environments, Science vol. 302, pp. 1967-1968, Dec. 2003.
Http://rice.tigr.org/tigr-scripts/CMR2/hit_to_all_db.spl?acc=TIGR02532.

* cited by examiner

*Primary Examiner*—Michael G Wityshyn
*Assistant Examiner*—Tiffany M Gough
(74) *Attorney, Agent, or Firm*—Reinhart Boerner Van Deuren s.s.

(57) ABSTRACT

Conductive nanowires, as are available from a range of bacteria species, methods of use and related device structures.

19 Claims, 8 Drawing Sheets

MICROBIAL NANOWIRES, RELATED SYSTEMS AND METHODS OF FABRICATION

This application claims priority benefit from provisional application Ser. No. 60/659,917, filed Mar. 9, 2005, the entirety of which is incorporated herein by reference.

The United States Government has certain rights to this invention pursuant to Grant Nos. S19000000300000DE-FC02-02ER63446 and S19000000100000DE-FG02-02ER63423 from the Department of Energy to the University of Massachusetts, Amherst.

BACKGROUND OF THE INVENTION

A major challenge in the field of nanoelectronics is the preparation of nanoscale materials, including nanowires, as electrical conduits between the nanocomponents of such devices. Proteins, in particular amyloid fibrils, have received much attention in that they provide desirable structural characteristics and can be readily adsorbed onto a range of suitable substrates. While such features are attractive, the typically low conductivity levels of protein nanowires limit their application. Metallization has been considered, but under industrial conditions can be deleterious to protein structure and integrity.

As a result, the design and fabrication of useful nanoelectronic materials has been an on going concern in the art. One approach is suggested and illustrated by the production of orderly self-assembled nanostructures in nature. Many bacteria have the ability to assemble small protein subunits, termed pilins, into one or more extracellular structured fibers, pilus or pili. Members of the family Geobacteraceae, for instance, produce pili to facilitate cellular oxidation-reduction mechanisms.

Further, mechanisms for extracellular microbial Fe(III) reduction have long been of interest in the art. The oxidation of organic matter coupled to Fe(III) reduction has a substantial influence on the degradation of organic matter and the geochemistry of iron, trace metals, and nutrients in many soils and sediments. Furthermore, such Fe(III) reducers can play an important role in the bioremediation of subsurface environments contaminated with organic pollutants or with metals such as uranium.

Some microorganisms, such as *Shewanella* and *Geothrix* species, may transfer electrons from the cell to the iron oxide surface via excretion of soluble electron-shuttling compounds whereas others, such as *Geobacter* species, require direct contact with the oxide surface. Previous studies demonstrated that *Geobacter metallireducens* specifically produced pili during growth on Fe(III) oxide, but not during growth on soluble, chelated Fe(III). Childers, S. E., Ciufo, S. & Lovley, D. R. *Geobacter metallireducens* accesses insoluble Fe(III) oxide by chemotaxis. *Nature* 416, 767-769 (2002). However, it remains uncertain whether such structures can be used for electrical conductivity.

BRIEF DESCRIPTION OF THE DRAWINGS

FIGS. 4A-F. In accordance with certain, non-limiting embodiments, conducting-probe atomic force microscopy analyses of *G. sulfurreducens* pili. (A) Topographic image of a pilus filament (indicated by arrows) and non-pilin goblular proteins that are also sheared off the cell surface. (B-C) Current image (B) of the field shown in (A) generated while applying a slow, triangular sweep bias voltage (C) to the tip during scanning. The strongest response was along the pilus filament (indicated by arrows) demonstrating that the pilus was a highly conductive path from the tip to the substrate. (D)

Overlay of height and current images showing selected regions (d1 and d2) across a pilus. High current was associated with the scan across the naked pilus, but no current was associated with the non-pilin material (d1, voltage ca. −401 mV) nor was it detected when the pilus was covered with non-pilin material (d2, voltage ca. −581 mV). (E) Height (left panel), current (middle panel) and voltage (right panel) line scan images of a pilus filament generated by disabling the slow axis in order to repeatedly scan horizontally across the same portion of the pilus. Under these conditions, the tip moved over the pilus filament much more slowly than in previous larger scans (A, B, and D), allowing the electronics to make a more spatially resolved image of the conductance across the pilus. The apparent increased width of the pilus in both topography and conductivity is an artifact resulting from convolution of tip dimensions during imaging and/or pilus deformation due to tip compression. (F) Linear correspondence between the current values recorded along the middle region of the pilus filament shown in (E) and the voltages applied (ranging from −600 mV to +600 mV). The size bar in each image represents 100 nm.

FIG. 5. In accordance with certain, non-limiting embodiments, phylogenetic analyses of geopilins. Amino acid sequence alignment of pilin domain proteins (GSU1496 (PilA) and GSU1776 (OxpG)) from *G. sulfurreducens* and pilins and pseudopilins from other bacteria were first generated using the Clustal X (1.8) program and manually optimized using the SeAl v. 2.0a11 Carbon program (University of Oxford). The alignment contained the conserved amino-terminal domain of pilins and pseudopilins and was used to infer the phylogenetic tree showing the phylogenetic distance between geopilins, pilins and pseudopilins from representative bacteria. The amino acid sequences of pilin subunits of *Shewanella oneidensis* strain MR-1, another metal reducer, and *Myxococcus xanthus* are also included. Metal reducers identified include *P. propionicus, G. sulfurreducens, G. metallireducens*, and *S. oneidensis*. Microorganisms closely related to *M. xanthus* also have been reported to reduce metals.

FIGS. 8A-F. In contrast to certain embodiments of this invention, CP-AFM analyses to *Shewanella oneidensis* MR-9 (A-C) and *Pseudomonas aeruginosa* strain K (D-F)pili. (A and C) Height images of pilus filaments. (B and D) Current maps obtained while applying a sweeping voltage (C and F) showing no detectable conductivity across the pilus filaments.

SUMMARY OF THE INVENTION

In light of the foregoing, it is an object of the present invention to provide microbial nanowires and/or related device structures, systems and methods for production and/or assembly, thereby overcoming various deficiencies and shortcomings in the nanoelectronic art. It will be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

It is an object of this invention to provide protein-based, naturally conductive nanowires without resort to metallization techniques or procedures.

It can be an object of this invention to provide conductive protein-based, nano-dimensioned wires or conductive components, produced and self-assembled in vitro or in vivo using a native host or engineered microorganisms.

It can be another object of this invention to provide one or more systems or methods for the production and self-assembly of protein-based nanowires, such microorganisms as can be, optionally, genetically modified to express pili with specific structural properties or chemical and/or electronic functionalities.

It can be another object of this invention to provide an electronic device structure and/or a circuit or electrical component thereof comprising at least one pilus or geopilus of the sort described herein, produced and/or self-assembled in vitro or in vivo using the native host or engineered microorganisms.

Other objects, features, benefits and advantages of the present invention will be apparent from this summary and the following descriptions of certain embodiments, and will be readily apparent to those skilled in the art having knowledge of various pili-producing microorganisms and related mechanisms for extracellular electron transfer. Such objects, features, benefits and advantages will be apparent from the above as taken into conjunction with the accompanying examples, data, figures and all reasonable inferences to be drawn therefrom alone or with consideration of the references incorporated herein.

The present invention relates to conductive pili and use thereof in various nanotechnological applications. More specifically, without limitation, the present invention also provides for the culture of bacteria producing conductive pili, isolation of such structures and, ultimately the fabrication of nano-dimensioned electronic circuit components.

Accordingly, in part, this invention can be directed to a method of preparing a conductive electronic circuit component. Such a method can comprise providing a bacterium capable of expressing a conductive proteinaceous pilus; providing a cultured medium conditioned for pilin production, such a medium comprising an electron acceptor; contacting the bacterium and the medium over a time sufficient for pilus assembly; and isolating the pilus from the medium. In accordance with this invention, pili are obtainable from bacteria known in the art to express conductive pilins and/or pili. More specifically, without limitation, such proteins can be encoded by the GSU 1496 gene. As would be understood by those skilled in the art made aware of this invention, such proteinaceous materials can be expressed by Geobacteraceae family members and other species, including but not limited to *G. sulfurreducens, G. metallireducens*, and *P. propionicus*. Phylogenetic analyses, of the type described herein, can be used to identify microorganisms having comparable genetic sequences or homologues thereof, or as could be engineered, encoding for conductive pilin/pilus formation and assembly.

As described more fully below, the conductive pili can be produced and/or obtained from systems comprising one of various strains of the aforementioned species, under appropriate culture conditions, with one or more suitable electron donor components and one or more suitable electron acceptor components, examples of the latter including but not limited to Fe(III) compounds (e.g., Fe(III) oxide). After a time sufficient for adequate protein expression and culture growth, pili can be sheared or separated from the cell surface, using various techniques known in the art, and used as described elsewhere herein. Pilins also can be produced and isolated in their soluble form using the native host or engineered microorganisms and assembled into pili in vitro.

In part, this invention can also comprise a method of using Geobacteraceae expression to prepare an electronic circuit component. Such a method can comprise providing at least one Geobacteraceae bacterium expressing one or more conductive proteinaceous pili; providing a culture medium conditioned for pilin production, such a medium comprising an electron acceptor; and contacting the bacterium or bacteria and the medium over a time sufficient for pilus assembly. As described above and illustrated more fully, below, in various embodiments of this invention, such proteinaceous materials can be expressed by various members of the Geobacteraceae family. In such or certain other embodiments, one or more pili can be isolated from the medium. If so, such a method can also comprise in vitro circuit assembly. Manifestation of certain embodiments can comprise application of a voltage across one or more pilus components.

Accordingly, this invention can also be directed to a range of nano-dimensioned electronic device structures, any of which can comprise a conductive circuit component comprising one or more conductive microbial pilus. Obtainable as described above, and in more detail, below, such components can be contacted with, adsorbed on or applied, connected and/or coupled to a suitable substrate material. A voltage source, alone or together with one or more other suitably-dimensioned circuit components, as would be known in the art, can be connected with or coupled to one or more pilus in the fabrication of a particular device structure.

DETAILED DESCRIPTION OF CERTAIN EMBODIMENTS

Figure 1:
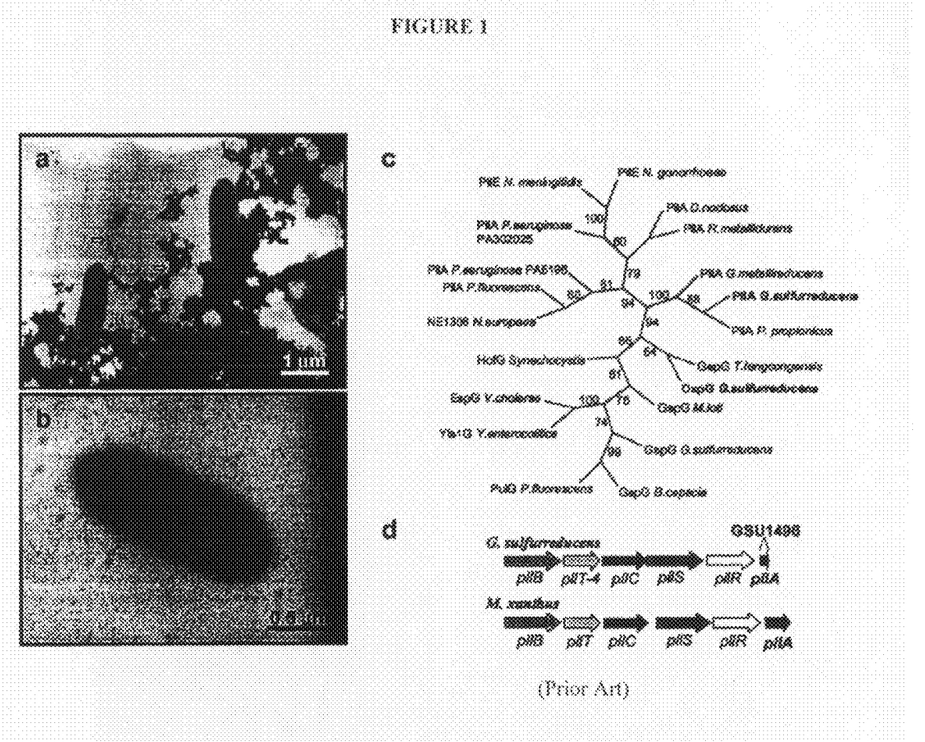
FIGS. 1A-D. In accordance with certain, non-limiting embodiments, identification of *G. sulfurreducens* pili. TEM analyses of negatively-stained cells of *G. sulfurreducens* grown with poorly crystalline Fe(III) oxides (A) or with soluble Fe(III) citrate (B) as sole electron acceptor. Pili (indicated by arrows) were detected in the presence of insoluble Fe(III) (A), but not soluble Fe(III) (B), and appear to form an intertwined network in association with the insoluble Fe(III) particles. (C) Unrooted phylogenetic tree derived from amino-terminal amino acid sequence alignments (see also FIG. 5) showing the relationship of the annotated *G. sulfurreducens* pilin domain proteins, encoded by GSU1496 and GSU1776, and pilin and pseudopilin proteins from other bacteria. Whereas the protein encoded by GSU1776 (OxpG) is related to bacterial pseudopilins, the protein encoded by GSU1496 (PilA) formed an independent line of descent with pilins from other members of the Geobacteraceae family. (D) Genomic organization of pilus biosynthesis genes surrounding GSU1496, a pilA homologue of *G. sulfurreducens* (top). This arrangement is analogous to the pil genes of *Myxococcus xanthus* (bottom).
Figure 2:
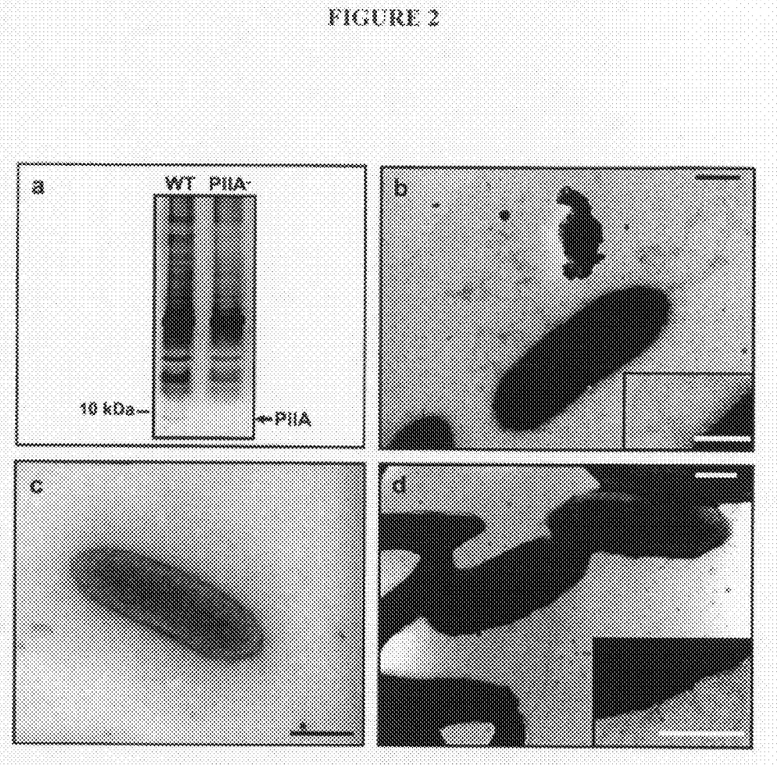
FIGS. 2A-D. In accordance with certain, non-limiting embodiments, *G. sulfurreducens* wild-type and pili-deficient mutant. (A) Denaturing gel of proteins from crude cell extracts showing the presence of the PilA precursor protein in the wild-type strain (identity confirmed by mass spectrometry) which was absent in the pilA-deficient mutant. Proteins were separated by denaturing (SDS) tricine-polyacrylamide gel electrophoresis (PAGE, 15%) and silver stained. The migration of a 10 kDa protein molecular weight marker is indicated. (B-D) Transmission electron microscopy analyses of negatively-stained cells of a wild-type (B), pilA-deficient mutant (C), and complemented mutant strain (D) of *G. sulfurreducens*. Cells were grown in medium with acetate and fumarate at 25° C. to induce pilin formation and negatively stained. Insets in (B) and (D) show details of pili produced by the wild-type and complemented mutant strains, respectively. Bars, 0.5 μm.

In order to evaluate electronic conduction and related pili-properties and characteristics, studies were conducted with a representative species in accordance with this invention, *Geobacter sulfurreducens*, a close relative of *G. metallireducens*, for which a genetic system and the complete genome sequence is available. See Coppi, M. V., Leang, C., Sandler, S. J. & Lovley, D. R. Development of a genetic system for *Geobacter sulfurreducens*. *Appl. Environ. Microbiol.* 67, 3180-7 (2001). Methe, B. A. et al. Genome of *Geobacter sulfurreducens*: metal reduction in subsurface environments. *Science* 302, 1967-1969 (2003). As in *G. metallireducens*, *G. sulfurreducens* produced pili during growth on Fe(III) oxide (FIG. 1A), but not soluble Fe(III) (FIG. 1B), and the pili were localized to one side of the cell (FIG. 2B). Pili formation could also be induced during growth on the alternative electron acceptor, fumarate, if the cells were grown at the suboptimal temperature of 25° C. (FIG. 2B), suggesting that pilin production in *G. sulfurreducens* is growth-regulated as it is in other bacteria. During growth, the Fe(III) oxides appeared to be specifically associated more with the pili than with the outer surface of the cell (FIG. 1A).

Figure 5:
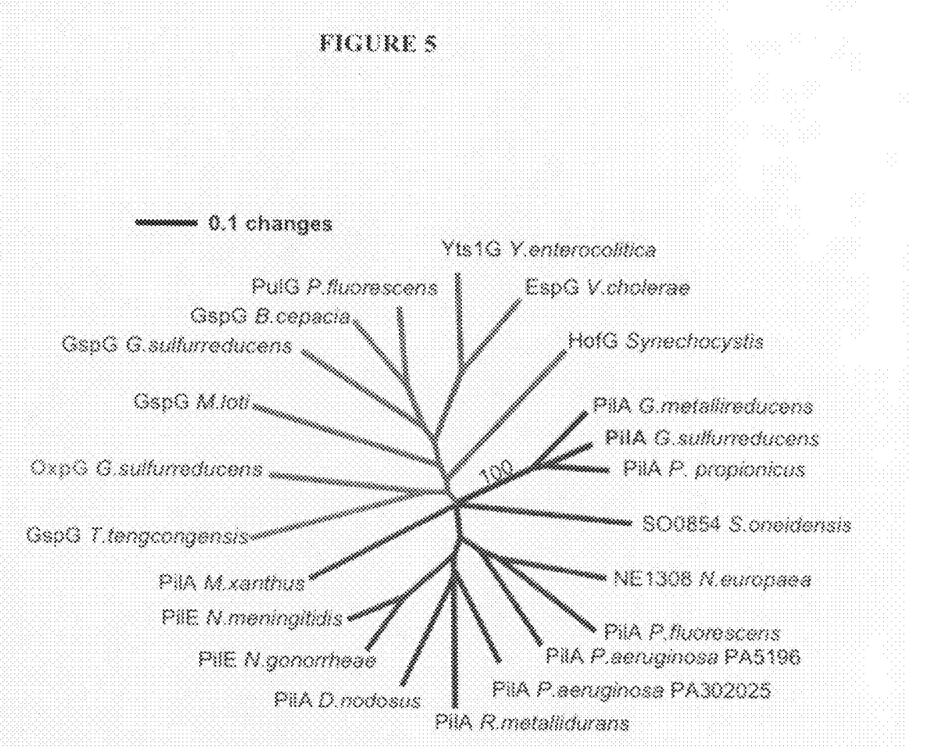

The genome sequence of *G. sulfurreducens* contained two open reading frames (ORF), GSU1496 and GSU1776, predicted to code for pilin domain proteins with the conserved amino-terminal amino acid characteristics of type IV pilins. Phylogenetic analyses placed the protein encoded by ORF GSU1776 among bacterial pseudopilins of type II secretion systems, and subsequent studies have confirmed the role of this gene, termed oxpG, in protein secretion to the outer membrane. The protein encoded by ORF GSU1496 formed an independent line of descent along with pilin subunits of other members of the Geobacteraceae such as *G. metallireducens* and *Pelobacter propionicus* (FIG. 1C). The predicted length of these *Geobacter* pilin proteins was considerably shorter than other bacterial pilin proteins (see FIG. 5A) and was restricted to the highly conserved, amino-terminal (N-t) domain of bacterial type IV pilins, which functions in inner membrane insertion, signal processing, and pilin polymerization, and forms the central helical core of the pilus filament. The degree of conservation of geopilins at this N-t region was lower than other bacterial pilins and, as a result, geopilins were phylogenetically distant from other bacterial pilins, including the SO0854 pilin of another metal reducer, *Shewanella oneidensis* (FIG. 5B). Homologues of genes required for pili formation and assembly in other gram-negative bacteria are upstream of the *Geobacter* pilA gene (FIG. 1D), in a genetic arrangement similar to that of the pili genes in *Myxococcus xanthus*, a delta-proteobacterium distantly related to *Geobacter*. These results suggest that the GSU1496 gene, as present in *G. sulfurreducens* (ATCC 51573), designated as PilA, encodes a pilin subunit.

Figure 3:
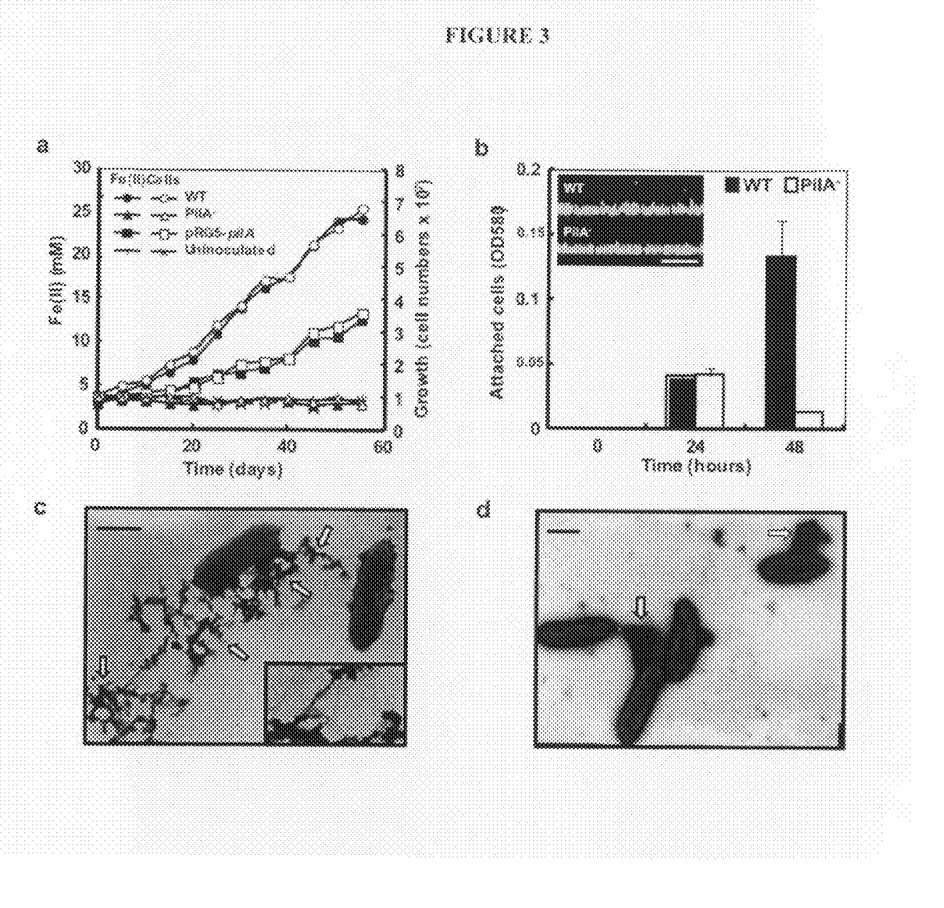
FIGS. 3A-D. Demonstrating various aspects of certain, non-limiting embodiments, a pili-deficient mutant is defective in Fe(III) oxide reduction but not in attachment to Fe(III). (A) Effect of a pilA mutation in the reduction of insoluble Fe(III) oxides. Cells of the wild-type (WT), ΔpilA mutant (PilA-) and complemented ΔpilA mutant (pRG5-pilA) strains were grown with poorly crystalline Fe(III) oxides as sole electron acceptor. Rates of Fe(III) oxide reduction were determined by measuring production of Fe(II) and growth was determined as cell counts of acridine orange-stained cells. (B) Cells of the wildtype (WT) and a pilA-deficient mutant (PilA-) were grown in the presence of Fe(III) oxide-coated coverslips, which induces pili expression in the WT strain. Biomass on the Fe(III) oxide was determined after staining the attached cells with crystal violet and measuring the optical density (OD) of the DMSO solubilized dye at 580 nm. Inset: Three-dimensional side view, generated by confocal scanning laser microscopy of the wild type and mutant biomass that attached to the Fe(III) oxide in the first 24 h. Substratum (Fe(III) oxide-coated coverslip) is located at the bottom of the images. Bar, 20 μm. (C-D) Transmission electron micrographs of negatively-stained cells of the WT (C) and PilA⁻ (D) cells that had been grown at 25° C. on fumarate to induce pili formation in the WT and then amended with poorly crystalline Fe(III) oxides. Fe(III) oxides (indicated by arrows) attached to the cell surface in both strains and also to pili in the WT. Inset in (C) shows a detail of WT pili with associated Fe(III) oxides. Bars, 0.5 μm.
Figure 6:
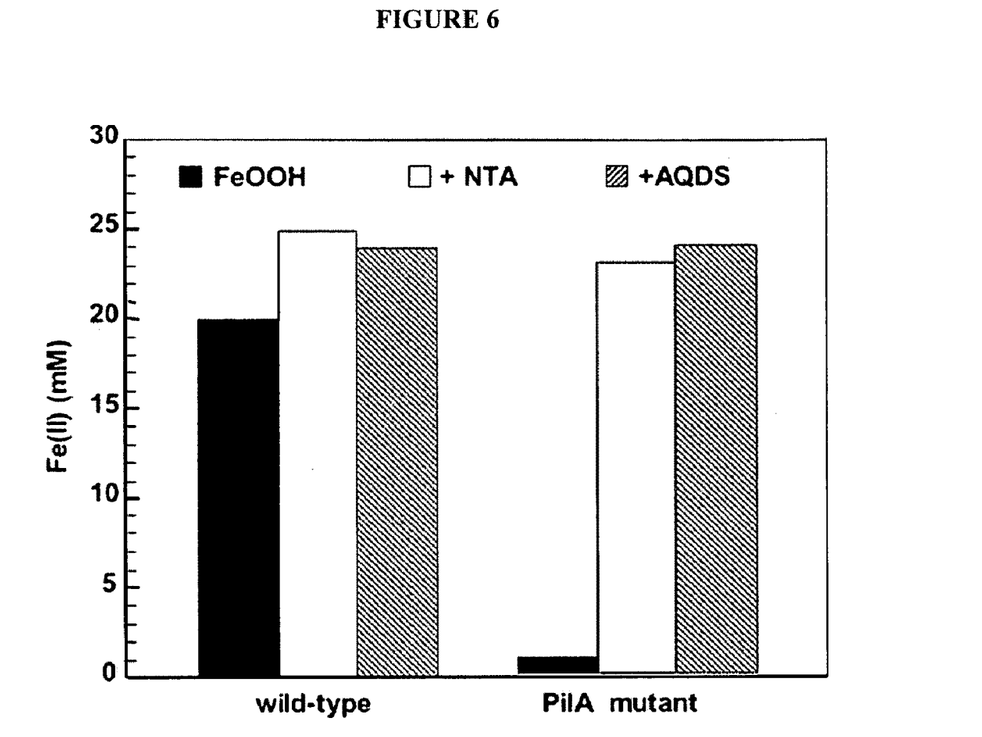
FIG. 6. Demonstrating various aspects of certain, non-limiting embodiments, restoration of Fe(III) oxide (FeOOH) reduction by the PilA⁻ mutant after media supplementation with 4 mM NTA, an Fe(III) chelator or 0.1 mM AQDS, an electron shuttle that alleviates the need for establishing contact with the insoluble Fe(III) oxides. The levels of soluble Fe(II), produced as a result of the reduction and growth on Fe(III) oxides were measured after 3 weeks of incubation with the insoluble electron acceptor.

When pilA was deleted, *G. sulfurreducens* failed to produce pili (FIG. 2C) and could no longer reduce insoluble electron acceptors such as poorly crystalline Fe(III) oxides (FIG. 3A) and Mn(IV) oxides (data not shown). In contrast, the mutant, as well as the wild-type, could reduce soluble electron acceptors, such as fumarate and Fe(III)-citrate. The mutant also grew in Fe(III) oxide medium if the chelator, nitrilotriacetic acid (NTA), was added in order to solubilize some of the Fe(III) (FIG. 6). Furthermore, Fe(III) oxide was reduced in the presence of anthraquinone-2,6-disulfonate (AQDS) (FIG. 6). AQDS serves as a soluble electron shuttle and transfers electrons between the cell surface and the surface of the Fe(III) oxide, alleviating the need for direct contact for Fe(III) oxide reduction. Complementation of the pilA mutation with a functional copy of the pilA gene in trans, restored the capacity for pili assembly (FIG. 2D) and the capacity for Fe(III) oxide reduction (FIG. 3A). These results demonstrated that *G. sulfurreducens* required assembly of functional pili in order to reduce insoluble Fe(III) oxides.

As known in the art, one known function of type IV pili in other microorganisms is establishing contact with surfaces. Fe(III) oxides are typically smaller than *G. sulfurreducens* (FIG. 1A), but it was possible to quantify the potential for attachment of Fe(III) to *G. sulfurreducens* by inoculating, fumarate-grown cells into medium in which Fe(III) oxide attached to glass coverslips was provided as the sole electron acceptor. Within the first 24 h, the cells of the pilA- deficient strain that were added initially attached to Fe(III) oxides as well as the wild-type (FIG. 3B) but whereas the wild-type grew on the Fe(III) oxide, as indicated by an increase in biomass on the Fe(III) oxide over the next 24 h, the pilA mutant could not grow, as demonstrated by a decrease in biomass (FIG. 3B). The pilA-deficient mutant did grow on the surface if fumarate was provided as an alternative electron acceptor (data not shown). These results demonstrate that pili are not required for Fe(III) oxides to attach to cells, yet further confirmed the necessity for pili for growth with Fe(III) oxides as the sole electron acceptor. Further evaluation of the nature of the association of the Fe(III) oxides with the cells revealed that, when Fe(III) oxides were added to fumarate-grown cells, the outer surface of the pilA-deficient mutant still had the ability to bind Fe(III) oxides (FIG. 3D) but in the wild-type there was substantial association of Fe(III) oxides with the pili (FIG. 3C). It has previously been hypothesized that *Geobacter* pili may mediate surface motility which might aid *G. sulfurreducens* in locating Fe(III) or Mn(VI) oxides, but no twitching motility of the wild-type cells was observed on Fe(III) oxide-coated glass surfaces.

Figure 4:
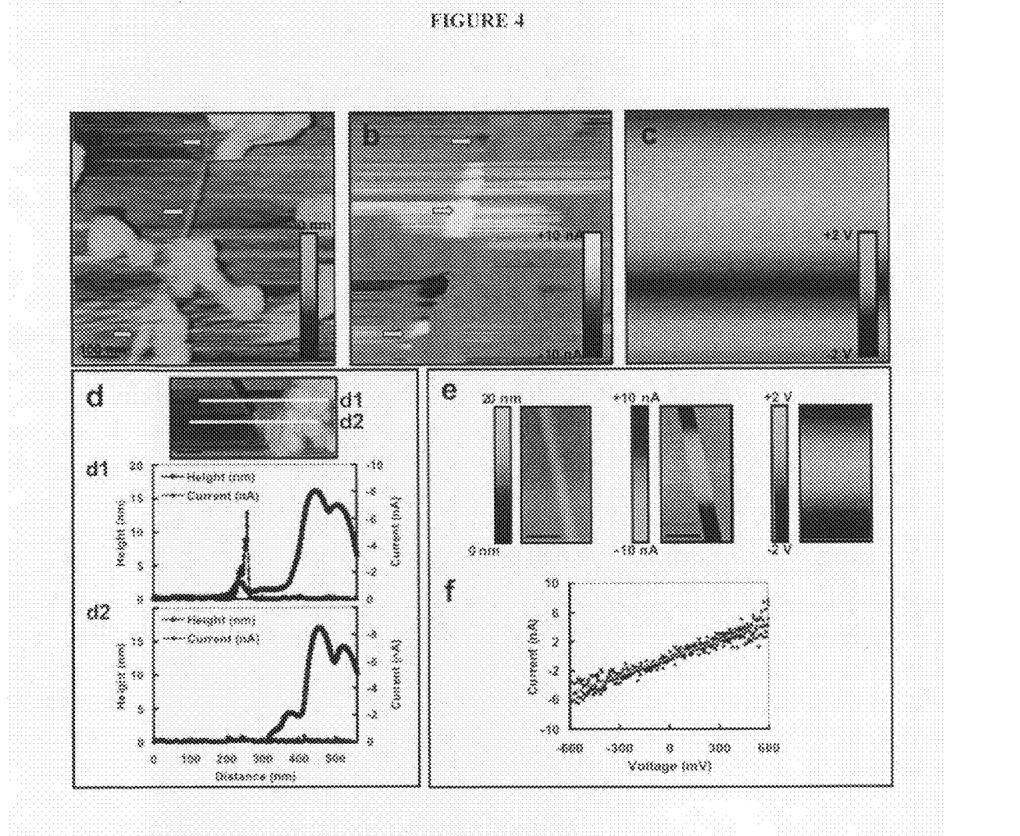
Figure 7:
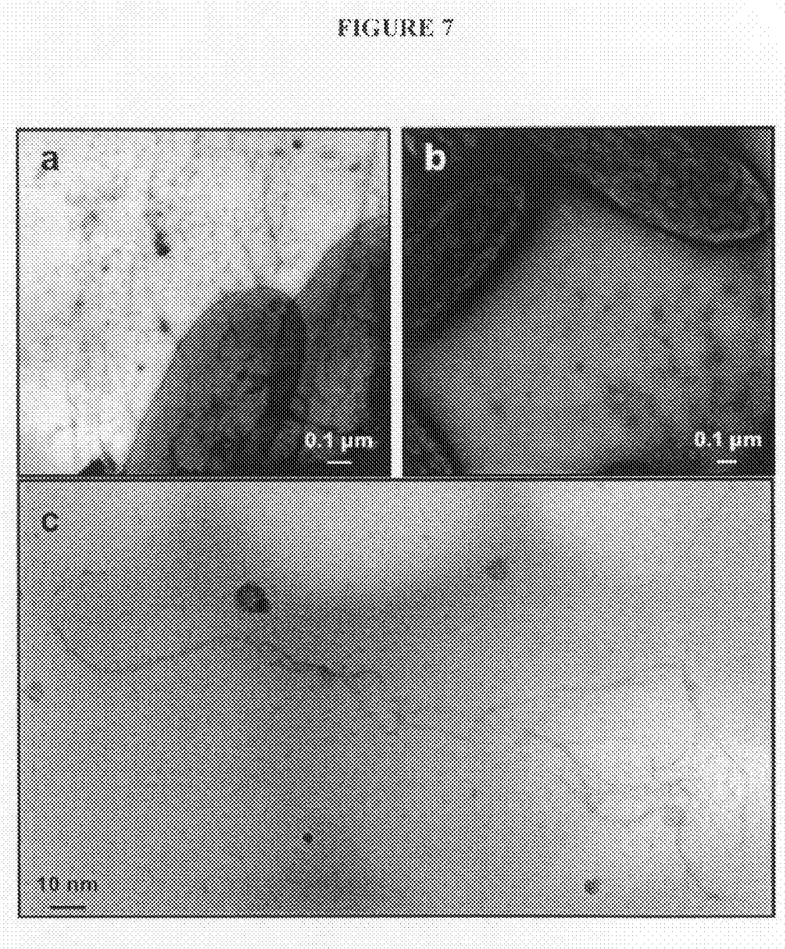
FIGS. 7A-C. In accordance with certain, non-limiting embodiments, TEM to negatively stained wild-type pill. (A-B) *G. sulfurreducens* cells expressing pill after 48 h of incubation at 25° C. in medium with fumarate. (C) Pili filaments that have been mechanically sheared off the outer surface of the wild-type strain of *G. sulfurreducens*. The wild-type pili preparations were analyzed by conducting AFM (FIG. 4) in order to study the electroconductive properties of *G. sulfurreducens* pill.
Figure 8:
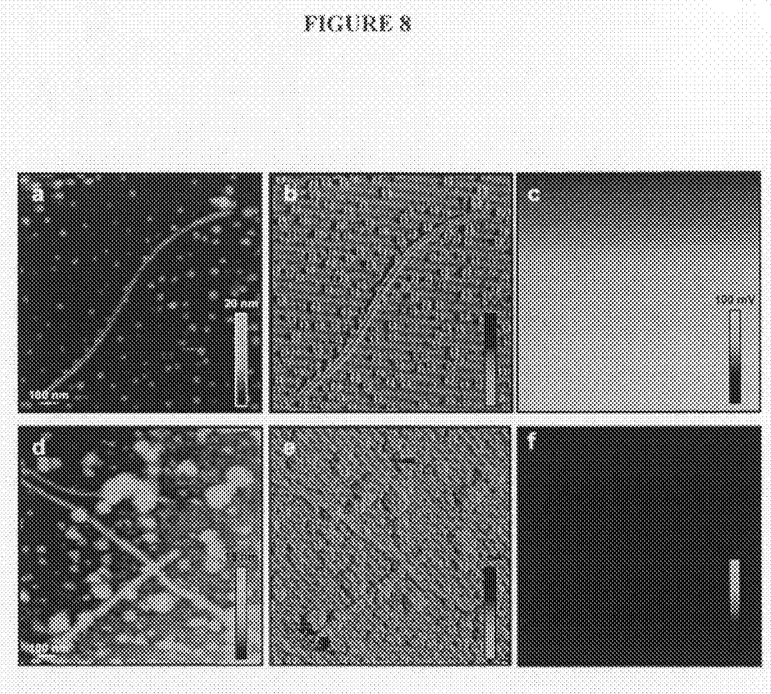

Electrical conductivity was measured to further confirm that pili have a direct role in electron transfer to Fe(III) oxides. Pili and other proteins released from the outer surface of *G. sulfurreducens* (FIG. 7) were immobilized on a graphite surface and analyzed with an atomic force microscope (AFM) equipped with a conductive tip and electronics that permitted mapping of the local conductance from the tip to the substrate (FIG. 4). Topographic analysis revealed pili as well as other, unidentified, more globular, proteins which were also sheared off the outer cell surface (FIG. 4A). Demonstrating use in conjunction with a voltage source, when a voltage was applied to the tip there was a strong current response along the pilus filament, which was positive when a positive voltage was applied and negative with a negative voltage (FIGS. 4B and C). In contrast, the non-pilin proteins had no detectable conductivity and in instances in which the non-pilin proteins covered the pili filaments, they insulated the pili from the conductive tip. This general response, initially observed in relatively large-scale scans (FIGS. 4A-C), was even clearer in cross sections in which high current was associated with the slight increase in topography associated with the pilin filament, but the higher topography, associated with non-pilin material, had no detectable current (FIG. 4D1). A scan across a portion of the pilin filament overlain by other material also yielded no detectable current (FIG. 4D2). Current line scans generated after applying different voltages while scanning the same region of a pilus demonstrated the linear, ohmic, correspondence between current and voltage applied (FIGS. 4E and F). When similar studies were carried out with pili from the metal reducer *S. oneidensis* or the non-metal reducer *Pseudomonas aeruginosa* no conductance was detected (FIG. 8).

These results demonstrate that the pili of *G. sulfurreducens*, representative species of this invention, are highly conductive, and are required to reduce Fe(III) oxides, as such components provide the electrical connection between the cell and the oxide surface. This contrasts with the nearly universal concept that outer-membrane cytochromes are the proteins which transfer electrons to Fe(III) oxide in Fe(III) reducers.

Conductive pili extend the electron transfer capabilities well beyond the cell surface. The pilus apparatus is anchored in the periplasm and outer membrane of gram-negative cells, thus offering the possibility of pili accepting electrons from periplasmic and/or outer membrane electron transfer proteins. These intermediary electron transfer proteins need not be the same in all organisms, consistent with the differences in cytochrome content and/or composition in different Fe(III) reducers. The likely function of the pili is to complete the circuit between these various intermediary electron carriers and the Fe(III) oxide.

In addition to serving as a conduit for electron transfer to Fe(III) oxides, pili could conceivably be involved in other electron transfer reactions. For example, pili of individual *Geobacter* cells are often intertwined, raising the possibility of cell to cell electron transfer via pili. These biologically produced nanowires might be useful in nanoelectronic applications with the possibility of genetically modifying pilin structure and/or composition to generate nanowires with different functionalities.

EXAMPLE OF THE INVENTION

The following non-limiting examples and data illustrate various aspects and features relating to the systems and/or methods of the present invention, including the production and assembly of microbial nanowires, components, circuits and related device structures, as are available through the techniques described herein. In comparison with the prior art, the present systems/methods provide results and data which are surprising, unexpected and contrary thereto. While the utility of this invention is illustrated through the use of several species, and pilins and/or pili expressed thereby, and electron acceptor components used therewith, it will be understood by those skilled in the art that comparable results are obtainable with various other species, whether natural or genetically modified and the pilins/pili expressed thereby, and corresponding electron acceptor agents, as are commensurate with the scope of this invention.

Bacterial strains and culture conditions. All *G. sulfurreducens* strains were isogenic with the wild-type strain PCA (ATCC 51573). A PilA− mutant strain was generated by replacement of the +61 to +159 coding region of the pilA gene (GSU1496) with a chloramphenicol cassette, as previously described in the literature. The pilA mutation was complemented in trans by introducing plasmid pRG5-pilA, a pRG5 derivative 29 carrying a wild-type copy of the coding region of pilA.

Cells were routinely cultured at 30° C. or 25° C. under strict anaerobic conditions in fresh water (FW) medium supplemented with acetate as electron donor and fumarate, Fe(III)-citrate, or poorly crystalline Fe(III) oxides (100 mmol/L) as the electron acceptor and with chloramphenicol (10 μg/ml) or spectinomycin (150-300 μg/ml) for cultures of the PilA− and pRG5-pilA strains, respectively.

Example 1

Conducting-Probe Atomic Force Microscopy analyses. Pili and other outer-surface proteins that were sheared from the cell surface by repeated passages through a 26 G hypodermic needle or by mechanical shearing with glass beads were allowed to adsorb onto the surface of freshly cleaved, highly oriented pyrolytic graphite for 20 min and fixed with 1% glutaraldehyde for 5 min. Fixed samples were washed twice with double deionized water and blotted dry. Samples were examined with a Veeco Digital Instruments Dimension™ 3100 AFM equipped with a Nanoscope IV™ Controller and a SAM III signal access module to enable electrical interface with the tip. A gold-coated AFM tip (nominal spring constant, 0.06 N/m; Veeco Inc.) was used for the imaging. The AFM was operated in contact mode with simultaneous tip-substrate conductivity mapping. While imaging, a slow "triangle-sweep" bias voltage was applied to the tip in reference to the graphite surface using a low-noise battery-powered ramping circuit. Current was measured with a DL Instruments 1211 current preamplifier.

Example 2

Phylogenetic analyses. Amino acid sequence alignments of *G. sulfurreducens* pilin domain proteins, GSU1496 and GSU1776, and pilin and pseudopilin proteins from other bacteria were generated using the Clustal X (1.8) program and manually optimized using the SeAl v. 2.0a11 Carbon program (University of Oxford). Phylogenetic trees were inferred from the optimized alignment by distance analysis using the PAUP 4.0 4a software package. Distance and branching order were determined by the neighbor-joining method using the BioNJ algorithm. See, Saitou, N. & Nei, M. The neighbor-joining method: a new method for reconstructing phylogenetic trees. *Mol. Biol. Evol.* 4, 406-25 (1987). Gascuel, O. BIONJ: an improved version of the NJ algorithm based on a simple model of sequence data. *Mol. Biol. Evol.* 14, 685-95 (1997). Bootstrap values were determined from 100 replicates by the neighbor method using the PAUP 4.0 4a software. The optimized alignment used to generate the phylogenetic tree is shown in supplementary FIG. 5. The *Pelobacter propionicus* pilA sequence was obtained from the Joint Genome Institute and can be accessed at wwwjgi.doe-.gov. The complete genome sequence of *G. sulfurreducens* can be found at www.tigr.org. There and other sequence used can be accessed with the following abbreviations: PilA, *Geobacter sulfurreducens* (gi:399996596); PilA, *G. metallireducens* (gi:23053459); OxpG, *G. sulfurreducens* (gi:41152675); GspG, *G. sulfurreducens* (gi:399995435); PilA, *P. propionicus* (Joint Genome Institute; wwwjgi.doe.gov); PilA, *Pseudomonas aeruginosa* PA302025 (gi:21629635); PilA, *Pseudomonas fluorescens* PfO-1 (gi:23058745); NE1308, *Nitrosomonas europaea* ATCC 19718 (gi:30249287); PilE, *Neisseria gonorrhoeae* FA1090 (gi:2921589); PilE, *Neisseria meningitidis* FAM18 (gi:2228578); PilA, *P. aeruginosa* PA5196 (gi:21464534); PilA, *Ralstonia metallidurans* (gi:15642724); SO0854, *S. oneidensis* (gi:24346423); PilA, *Myxococcus xanthus* (gi:950654); EspG, *V. cholerae* El TorN16961 (gi:15642724); GspG, *Mesorhizobium loti* MAF 303099 (gi:13475692); GspG, *Burkholderia cepacia* KF1 (gi:22978954); PilA, *Dichelobacter nodosus* N2 (gi:16118465); PulG, *P. fluorescens* PfO-1 (gi:23059410); GspG, *Thermoanaerobacter tengcongensis* MB4T (gi:20807714); HofG, *Synechocystis* sp. PCC6803 (gi:16330343); Yts1G, *Yersinia enterocolitica* WA-314 (gi:27529239).

Example 3

Polyacrylamide Gel electrophoresis (PAGE) and protein identification. Crude extracts for SDS-PAGE analyses were prepared from cells grown in FWacetate/fumarate medium using Fe(III) oxide-coated vessels. After 72 h, the cells were collected, washed in phosphate buffer saline and resuspended in phosphate buffer saline. Proteins in crude cell extracts were separated in 15% SDS-Tricine polyacrylamide gels, as known in the literature, and visualized by Mass Spectrometry compatible silver staining (Invitrogen, Carlsbad, Calif.). Silver-stained protein bands were excised, destained and digested with trypsin and the masses of the peptides was determined with a tandem mass spectrometer after separation by microcapillary liquid chromatography (University of Massachusetts-Amherst). Peptide masses were analyzed using the Protein Prospector software (University of California, San Francisco). See, Clauser, K. R., Baker, P. & Burlingame, A. L. Role of accurate mass measurement (+/−10 ppm) in protein identification strategies employing MS or MS/MS and database searching. Clauser, K. R., Baker, P. & Burlingame, A. L. Role of accurate mass measurement (+/−10 ppm) in protein identification strategies employing MS or MS/MS and database searching. *Anal. Chem.* 71, 2871-82 (1999).

Example 4

Attachment assays. For Fe(III) oxides attachment assays, cells were grown in FW-acetate medium in the presence or absence of the soluble electron acceptor, fumarate, and incubated at 30° C. with Fe(III) oxide-coated borosilicate coverslips. The bacterial biomass that attached to the Fe(III)-coated coverslips was stained with 1% crystal violet, and the cell-associated dye was then solubilized in dimethyl sulfoxide (DMSO) and quantified by measuring the OD580 of the dye-DMSO solution. Attached cells also were stained with the BacLight™ fluorescence dyes (Molecular Probes) and examined with a Zeiss LSM510 inverted confocal scanning laser microscope (CSLM) equipped with a 63× long working distance objective. Attachment also can be assayed by growing cells of the WT and PilA-mutant under pili-inducing conditions in the absence of Fe(III) oxides (i.e., growth in FW-acetate/fumarate medium and incubation at 25° C. for 48-72 h) and transferring the cells to FW medium with poorly crystalline Fe(III) oxides (100 mmol/L) and with no electron donor. After 24 h of incubation at 25° C., cells were negatively stained with uranyl acetate and visualized by transmission electron microscopy.

Example 5

Various pili biochemical and electronic properties can be modified, as would be understood by those skilled in the art made aware of this invention. For instance, one such method comprises genetic modification of pilA encoding the pilin subunit of *G. sulfurreducens*, to target amino acid residues of the subunits and resulting pili filaments. Alteration of amino acid sequence can also be used to modify secondary and ternary protein structure. (See, e.g., Daggett, V. & Fersht, A. The present view of the mechanism of protein folding. *Nat. Rev. Mol. Cell Biol.* 4, 497-502 (2003), the entirety of which is incorporated herein by reference.)

Example 6

Likewise, as would be understood in the art, genetic and biochemical modifications can be directed to generate chemical tags and targets on pili filaments for the generation of hybrid devices with different functionalities. For example, pilin derivatives can be genetically modified to contain exposed cysteine residues without affecting filament assembly kinetics. Various chemical species specifically and/or covalently interacting with the cysteine sulfhydryl group can be used to modify the filament surface (e.g., with conductive components such as gold nanoparticles; see, Scheibel, T. et al. Conducting nanowires built by controlled self-assembly of amyloid fibers and selective metal deposition. *Proc. Natl. Acad. Sci. USA* 100, 4527-32 (2003), the entirety of which is incorporated herein by reference). Likewise, other structural variations can be introduced for subsequent chemical, structural or functional modification of the pilins/pili and/or resulting nanowires or electrical components.

While the principles of this invention have been described in connection with specific embodiments, it should be understood clearly that these descriptions are provided only by way of example and are not intended to limit, in any way, the scope of this invention. For instance, the conductive microbial components of this invention can be readily and economically produced for use in the fabrication of a range of electronic nanocomponents or related device structures. Whether obtained from native sources or genetically modified, produced in vivo or assembled in vitro (see, Audette, G. F., Irvin, R. T., and Hazes, B. Crystallographic analysis of the *Pseudomonas aeruginosa* strain K122-4 monomeric pilin reveals a conserved receptor-binding architecture. *Biochemistry* 43, 11427-35 (2004); Chapman, M. R., Robinson, L. S., Pinkner, J. S., Roth, R., Heuser, J., Hammar, M., Normark, S., and Hultgren, S. J. Role of *Escherichia coli* curli operons in directing amyloid fiber formation. *Science* 295, 851-5 (2002)), applications include but are not limited to development of nanowires with electronic properties (e.g., metallic or semi-conducting) for control of electron charge in a range of nanodevices, including but not limited to electrically-based biological and/or chemical biosensors. Likewise, the conductive properties illustrated above can be used for the direct electrical detection of certain macromolecules of biological interest. (See, Cui, Y., Wei, Q., Park, H. & Lieber, C. M. Nanowire nanosensors for highly sensitive and selective detection of biological and chemical species. *Science* 293, 1289-92 (2001).) Such nanosensors can find practical application in the detection of glucose levels in diabetic patients, the measurement of hormonal levels, and DNA detection in forensic settings. It is also possible to use such conductive nanocomponents, as electronically or conductively modified, for selective detection of biological or chemical species at the single particle level (e.g., stochastic sensing). For example, geopili of the sort described herein can be modified with antibodies that bind biotopes in biological samples, such as pathogenic bacteria or viruses. The conductance changes upon binding or unbinding of the biological samples to the antibodies can be measured electrically. See, Patolsky, F. et al. Electrical detection of single viruses. *Proc. Nat'l. Acad. Sci. USA* 101, 14017-22 (2004). Each of the aforementioned references is incorporated herein by reference in its entirety.

We claim:

1. A method of preparing a conductive electronic circuit component, said method comprising:
   providing a bacterium expressing a conductive proteinaceous pilus;
   providing a culture medium conditioned for conductive pilin production, said medium comprising an electron acceptor;
   contacting said bacterium with said medium over a time sufficient for assembly of said pilus;
   isolating said conductive pilus from said medium; and
   coupling said conductive pilus to a circuit component.

2. The method of claim 1 wherein said pilus is encoded by the GSU1496 gene.

3. The method of claim 2 wherein said pilus is expressed by a *Geobacteraceae* bacterium.

4. The method of claim 2 wherein said bacterium is selected from *G. sulfurreducens*, *G. metallireducens*, and *P. proprionicus*.

5. The method of claim 1 wherein said coupling is in vitro.

6. The method of claim 5 wherein said pilus is contacted with a substrate component.

7. The method of claim 1 wherein said medium comprises an Fe(III) compound.

8. The method of claim 7 wherein said compound is Fe(III) oxide.

9. A method of using Geobacteraceae expression to prepare an electronic circuit component, said method comprising:
   providing a Geobacteraceae bacterium expressing at least one conductive proteinaceous pilus;
   providing a culture medium conditioned for conductive pilin production, said medium comprising an electron acceptor;
   contacting said bacterium and said medium over a time sufficient for assembly of said pilus;
   removing said conductive pilus from said bacterium; and
   coupling said conductive pilus to a circuit component.

10. The method of claim 9 wherein said Geobacteraceae bacterium is selected from *G. sulfurreducens* and *G. metallireducens*.

11. The method of claim 10 comprising isolation of said pilus from said medium.

12. The method of claim 11 wherein said coupling is in vitro.

13. The method of claim 12 wherein a voltage can be applied across said pilus.

14. The method of claim 9 wherein said medium comprises an Fe(III) compound.

15. The method of claim 14 wherein said compound is Fe(III) oxide.

16. A nanodimensioned electronic device comprising a conductive circuit component comprising a proteinaceous pilus, said pilus the expression product of a bacterium comprising the GSU1496 gene, said pilus coupled in vitro to a voltage source.

17. The device of claim 16 wherein said pilus is expressed by a Geobacteraceae bacterium.

18. The device of claim 16 wherein said bacterium is selected from *G. sulfurreducens, C. metallireducens*, and *P. proprionicus*.

19. The device of claim 16 further comprising a substrate component.

* * * * *